US006337994B1

United States Patent
Stoianovici et al.

(10) Patent No.: US 6,337,994 B1
(45) Date of Patent: Jan. 8, 2002

(54) SURGICAL NEEDLE PROBE FOR ELECTRICAL IMPEDANCE MEASUREMENTS

(75) Inventors: Dan Stoianovici, Baltimore; Louis R. Kavoussi, Lutherville; Mohamad Allaf; Stephen Jackman, both of Baltimore, all of MD (US)

(73) Assignee: Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/300,277

(22) Filed: Apr. 27, 1999

Related U.S. Application Data

(60) Provisional application No. 60/083,619, filed on Apr. 30, 1998.

(51) Int. Cl.[7] ................................................. A61B 5/05
(52) U.S. Cl. ....................... 600/547; 606/130; 600/372; 600/373; 600/424; 433/32; 433/27; 433/72
(58) Field of Search ................................. 600/547, 372, 600/373, 424; 606/130; 433/32, 27, 72

(56) References Cited

U.S. PATENT DOCUMENTS

| 4,140,109 | A |   | 2/1979 | Savic |
| 4,372,315 | A |   | 2/1983 | Shapiro et al. |
| 4,951,682 | A | * | 8/1990 | Petre .......................... 128/713 |
| 5,080,586 | A | * | 1/1992 | Kawai .......................... 433/32 |
| 5,335,668 | A | * | 8/1994 | Nardella ..................... 128/734 |
| 5,904,651 | A | * | 5/1999 | Swanson et al. ........... 600/407 |

* cited by examiner

Primary Examiner—Marvin M. Lateef
Assistant Examiner—Jeoyuh Lin
(74) Attorney, Agent, or Firm—Nixon & Vanderhye PC

(57) ABSTRACT

An electrical impedance probe is provided that includes a surgical needle. In an exemplary embodiment, the probe is a two-part trocar needle designed to acquire impedance measurements at its tip. The impedance measurements are representative of the local properties of a biological substance at the needle tip. Thus, the probe may be used to confirm needle insertion into a desired anatomical target or to identify the nature of the cells surrounding the tip of the needle. In urology, this sensor is used for confirming the needle insertion into the urinary tract, for localizing renal cell carcinoma, and prostate cancer.

14 Claims, 5 Drawing Sheets

SURGICAL NEEDLE PROBE FOR ELECTRICAL IMPEDANCE MEASUREMENTS

This application claims the benefit of U.S. Provisional Application Serial No. 60/083,619, which was filed Apr. 30, 1998, the disclosure of which is incorporated herein by this reference.

BACKGROUND OF THE INVENTION

1. Field of the Invention

The present invention relates to a probe for electrical impedance measurement and more particularly to a surgical needle construction for providing electrical impedance measurements to confirm or monitor the location of the needle tip within a patient's body.

2. Description of the Related Art

Surgical needles, such as trocar needles, are known and used during surgical procedures to access target body tissue or a target body cavity for observation, treatment, biopsy, and the like. Typically, trocar needles comprise an outer cannula and an inner stylet. The stylet typically has a sharp, pointed tip for skin and tissue penetration and the outer cannula defining a channel to provide subsequent access for endoscopic examination, biopsy, or the like. Sometimes the cannula has a sharp distal edge, in which case the stylet may be a blunt obturator and/or inner cannula.

The insertion of conventional trocar needles can be problematic. Indeed, the surgeon must estimate the location of the trocar needle tip during insertion. This may result in the undesirable accidental puncture of anatomical structures as the needle is being inserted and the surgeon may have difficulty in confirming arrival at a desired anatomical target.

BRIEF SUMMARY OF THE INVENTION

Because conventional trocar insertion methods are imprecise and may be risky, it is an object of this invention to provide a surgical needle, such as a trocar needle, that allows the surgeon to monitor the path of needle insertion, to confirm needle insertion into a desired anatomical target, and/or to identify the nature of cells surrounding the tip of the trocar needle.

The foregoing object is realized by providing a two-part trocar needle designed to acquire impedance measurements at its tip. Such impedance measurements characterize the biological substance at the needle tip. Thus, the impedance measurements provided by the trocar needle of the invention may be used to confirm needle insertion into a desired anatomical target and/or to identify the nature of the biological material surrounding the tip of the needle, to monitor the path of the needle, or for diagnostic purposes. In urology, an impedance sensor provided in accordance with the invention may be used to confirm needle insertion into the urinary tract and for localizing, e.g., renal cell carcinoma.

Thus, the foregoing and other objects are realized in accordance with the present invention by providing a surgical probe for obtaining impedance measurements, comprising a hollow trocar sleeve having an electrically conductive portion defining a first electrode adjacent its distal end, and means, e.g., the wall of the trocar sleeve or a portion thereof, or a lead therein, for electrically connecting the electrically conductive portion to a proximal end portion of the sleeve; a stylet having an electrically conductive portion defining a second electrode adjacent its distal end, and means for electrically connecting the electrically conductive portion to a proximal end portion of the stylet; an electrical insulator disposed between the trocar sleeve and the stylet; and an impedance meter electrically coupled to the electrodes, for indicating the impedance of a biological substance contacting the electrodes. It should be recalled, that as noted above, a trocar needle assembly that has two (or more) parts may have a sharp pointed stylet and/or an outer cannula terminating in a sharp edge. Where the outer cannula is adapted to piercing the material through which the trocar is inserted, the inner stylet can be but is not necessarily pointed; it may be a blunt obturator and/or inner cannula. Therefore, references to stylet herein are intended to refer to the structure disposed within the outer cannula, but are not to be limited to a sharp, pointed component unless so specified.

Also and alternatively, the objects of the invention may be realized by providing a diagnostic impedance measuring system comprising: an elongate tissue-penetrating needle, a first portion of the distal end of said tissue penetrating needle being electrically conductive; at least one electrode structure disposed adjacent the distal end of the needle and axially spaced from the first portion thereof, the first portion and the at least one electrode being electrically connected to an impedance measuring device for measuring an electrical impedance of a biological substance contacting said first portion and said electrode.

The objects of the invention are also realized by inserting an impedance probe of the type described above into a patient's body, measuring the impedance between the electrodes, and confirming the location of the distal tip (within a region of interest and/or the identity of the biological substance at the tip of the probe from the measured impedance.

BRIEF DESCRIPTION OF THE DRAWINGS

These, as well as other objects and advantages of this invention, will be more completely understood and appreciated by careful study of the following more detailed description of a presently preferred exemplary embodiments of the invention taken in conjunction with the accompanying drawings, in which.

DETAILED DESCRIPTION OF THE PRESENTLY PREFERRED EXEMPLARY EMBODIMENTS

The designs of the herein described exemplary needle probes are based on the common design of trocar needles.

The trocar needle is constructed of two main parts: an outer tubular shell or barrel and an inner stylet that is disposed within the outer shell. Both parts are normally and preferably constructed of metal. To define an electrical impedance needle probe in accordance with the invention, an electrically insulating layer is provided between the barrel and the stylet of the assembly. In the embodiments illustrated in FIGS. 1 and 6, the inner stylet has a sharp point at its distal end, consistent with the presently preferred implementation of the invention. As will become apparent, however, the invention may be implemented with a trocar-type assembly having an outer cannula with a sharp distal edge, in which case the inner stylet may be blunt tipped.

Figure 1:
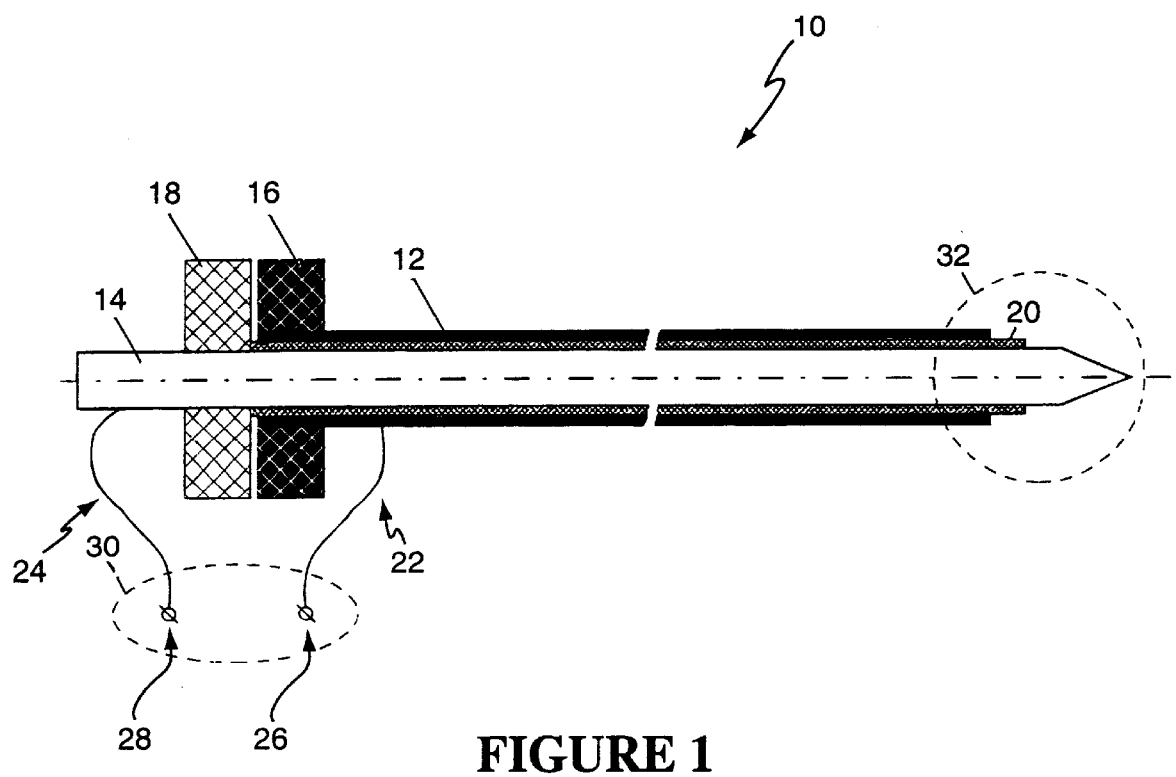
FIG. 1 is a schematic illustration of a longitudinal cross-section of an exemplary embodiment of a trocar needle probe for electrical impedance measurements provided in accordance with the present invention.

Thus, a probe embodying the present invention is schematically illustrated in axial cross section in FIG. 1. In the illustrated embodiment, the probe 10 presents a two-part construction comprising the outer sleeve or needle barrel 12 and the inner stylet 14. The tip of the needle is pointed at the sharp stylet tip and the head of the needle comprises the head of the barrel 16 and the head of the stylet 18. The heads 16 and 18 are attached so that the barrel 12 and the stylet 14 are assembled and the stylet remains within the barrel during needle insertion.

The barrel 12 and stylet 14 are constructed of electrically conductive materials, e.g. metal, whereas the heads 16 and 18 are constructed of an electrical insulator, such as plastic. A non-conductive material 20 is disposed between the inner stylet 14 and the outer sleeve or barrel 12 so as to electrically isolate the stylet and the barrel sleeve. This insulator 20 is preferably deposited on or securely applied to the stylet 14 such that they form a substantially unitary structure for simultaneous disposition in and removal from the barrel. The attachment at heads 16 and 18 facilitates easy detachment so that the stylet 14, including the insulation 20, may easily be removed from the barrel 12. Moreover, providing the insulator on the stylet maximizes the lumen of the barrel for the conduct of further surgical procedures.

With the addition of the insulating layer, the electrically conductive barrel 12 and the stylet 14 are electrically separated so that their distal ends define two electrodes that are electrically insulated from one another. For electrical impedance measurements, the distance between the electrodes plays a significant factor. With the proposed impedance measuring probe, the distance between the electrodes is constant whereby the probe provides consistent and repeatable measurements. As will be appreciated, however, an initial calibration will be required for any change in the disposition or geometry of the electrode structures provided by the sleeve and stylet.

Insulation layer 20 allows the barrel 12 and the stylet 14 to respectively serve as connectors for connecting the electrodes defined by their distal ends to the needle heads for ultimate attachment to an impedance meter. Thus, in the illustrated embodiment, a first lead 22 extends from the proximal end of trocar sleeve 12 and a second lead 24 extends from the proximal end of stylet 12. The leads are desirably provided with suitable connectors 26, 28 for coupling to complementary connectors or leads of a suitable impedance meter 30, or a meter is provided with leads terminating in alligator clips (see FIG. 7) can simply be clipped directly to the stylet and barrel, and/or to leads extending therefrom.

While inserting the tip of the needle into a substance, i.e. an anatomical target, the electrical impedance of the substance 32 surrounding the tip may thus be acquired by connecting an impedance meter 30 close to the needle head.

Thus, this simple probe structure allows the measurement of impedance at the needle tip by connecting a suitable measurement instrument adjacent the needle head. As is apparent, the inventive probe structure 10 may easily be implemented as an add on to current trocar needles. Moreover, the simple configuration allows the construction of high gauge, thin needles. Furthermore, any conventional impedance measurement instrument 30 attached to the needle probe 10 may be used to acquire the data.

In their experiments, the inventors used the needle impedance probe schematically depicted in FIG. 1 in conjunction with a multi-frequency LCR meter (HP 4275A) to determine the electrical properties of the substance at the needle tip. LCR meters apply a low-voltage sinusoidal signal of high frequency to the electrodes and measure the amplitude and the phase shift of the response signal. Based on these measurements the meter calculates and displays the impedance measurement as well as the individual components of the impedance: R-resistance, C-capacitance, and L-inductance. For biological measurement the value of interest is the resistivity $\rho$ (or conductivity $1/\rho$) of the substance/tissue at the needle tip. Its value may be derived from the resistance measurement.

$$R = K\rho \qquad \text{(Eq. 1)}$$

where, R is the resistance, $\rho$ is the resistivity, and K is a constant that depends on the geometry of the probe; referred to herein below as the needle probe calibration constant. The constant K should be estimated for the needle-probe by performing the measurement into a known resistivity solution.

Figure 2:
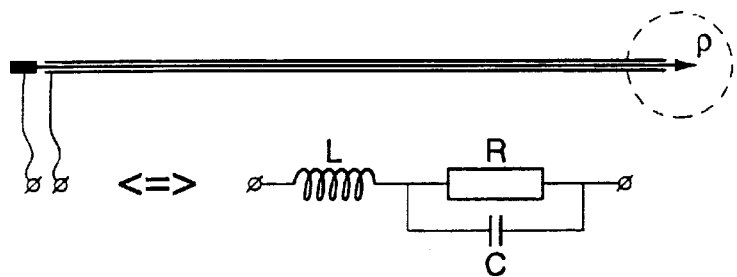
FIG. 2 is a schematic illustration of an equivalent electrical circuit for the probe of FIG. 1.

In order for the LCR meter to provide correct measurement of the desired resistance component R it is critical to choose the proper equivalent electrical circuit that is being measured. The inventors found that the needle probe of FIG. 1 is electrically equivalent to an inductor, resistor and capacitor circuit as presented in FIG. 2.

The inductor L is mainly due to the connecting wires, the capacitor C to the coaxial design of the needle-probe as well as the cabling, while the resistor R is mainly due to the resistivity $\rho$ of the substance measured. In the experiments the inductor L was insignificant for the frequency range addressed (10 KHz–4 MHz) and it could be neglected. For practical reasons, the electrical circuit that models the needle-probe is a parallel resistor and capacitor circuit. The use of this simpler model with only two components has the advantage of providing results for the R and C values at each measurement. Explicit values of the R and C components are extracted from the impedance and phase shift measurements using the well-known formulas of the parallel RC circuit:

$$Z = \frac{R}{\sqrt{1 + \omega^2 C^2 R^2}} \; [\Omega] \qquad \text{Eq. 2}$$

$$\alpha = -\tan^{-1}(\omega CR) \; [0 \le \alpha \le \pi]$$

where, Z is the impedance, $\omega = 2\pi f$, f is the frequency of the excitation signal $E(t) = E_0 \sin(\omega t)$, and $\alpha$ is the phase shift. The LCR meter measures Z and $\alpha$ and uses equation Eq.2 to calculate and display the value of R. The resistivity $\rho$ of the tissue/solution is then calculated using Eq.1 with K predetermined from calibration experiments in standard resistivity solutions.

Figure 3:
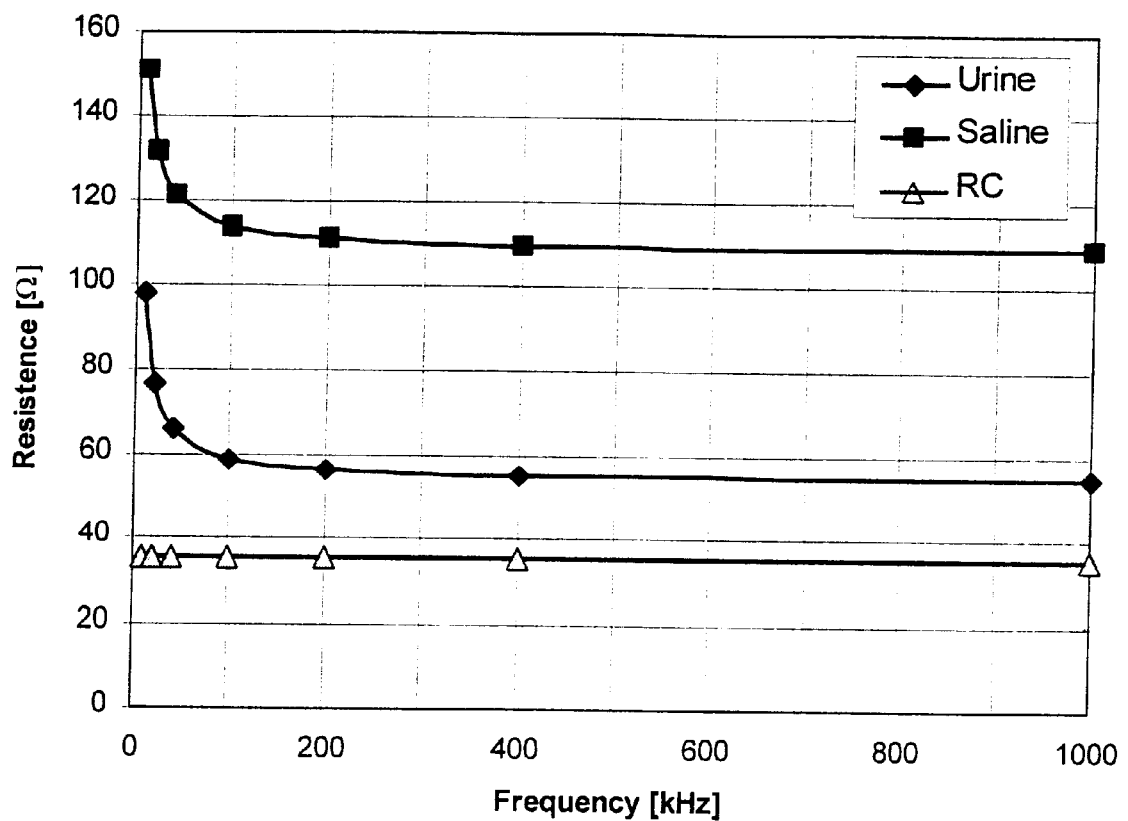
FIG. 3 is a graph depicts the results of resistance measurements as a function of the frequency of the excitation signal.

FIG. 3 depicts the results of resistance measurements as a function of the frequency of the excitation signal. The first two plots (Urine and Saline) used the needle probe immersed in urine and saline respectively whereas the third plot (RC) used a parallel resistor and capacitor circuit connected to the LCR meter. A parallel RC circuit model was used to separate resistance values. The RC plot, for which the assumed RC model was perfect, revealed very small variations of the measured resistance with frequency. For the needle-probe, however, there was significant variation of resistivity in the low-frequency range. This was explained and experimentally observed by the plating phenomenon of the electrodes. Above a certain frequency ($f \geq 300$ kHz) plating was over-passed and resistance values exhibited minimal variation. In conclusion, the RC model of the needle probe proved to be valid for frequencies above 300 kHz.

Figure 4:
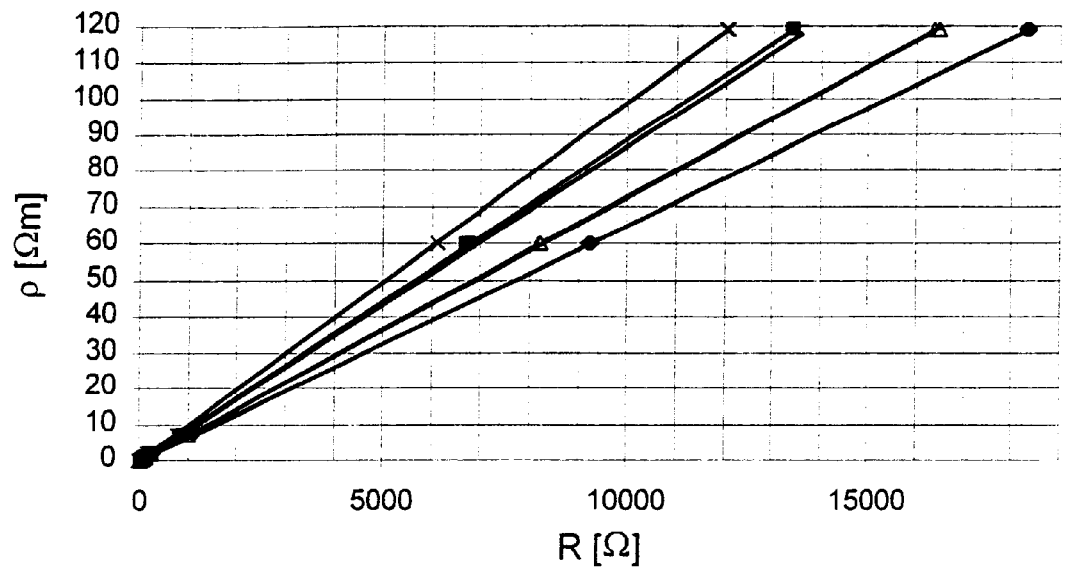
FIG. 4 is a graph of Resistivity vs. Resistance for various needle-probes showing the needle-probe calibration constant.

The constant K depends on the geometry of the needle tip, specifically on the size and distance between the "electrodes". To verify equation Eq.1 the inventors performed experiments with five needle-probes presenting geometry variations by measuring the resistance R at 200, 400, and 1000 kHz for six known resistivity solutions between 0.125 and 120 $\Omega$m. The results are depicted in FIG. 4.

The graphs show the linearity of the resistivity $\rho$ and resistance R as given by the formula in Eq.1. It may also be observed that different probes present different calibration constants K. The constant K may easily be calculated with equation 1 for one experiment in a known resistivity solution or over multiple experiments by linearly interpolating all $\rho$-R pairs for the given needle.

Figure 5:
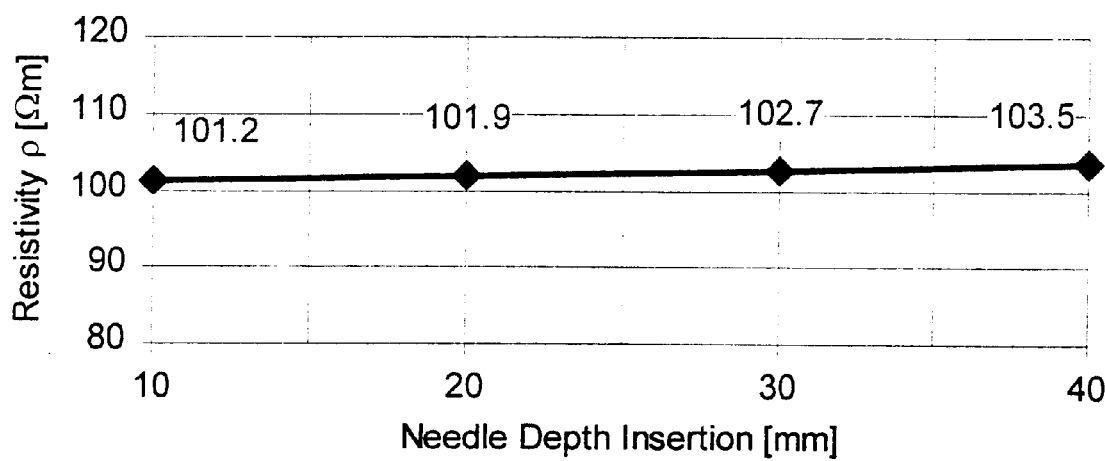
FIG. 5 is a graph of the dependence of measured resistivity on the needle-probe depth of insertion for the preferred embodiment of FIG. 1.

In all the experiments above, the needle depth of insertion into the solution was maintained constant. As is well known, the calibration constant K depends not only on the distance between the electrodes but also on the surface area of the electrodes. In the design of the needle-probe presented in FIG. 1, the electrode represented by the barrel 12 of the needle 10 may not be completely be immersed into the measured substance/tissue, thus its area is a function of the depth of insertion. The dependence of measured resistivity on the depth of insertion of the needle-probe into the solution/tissue is presented in FIG. 5.

Figure 6:
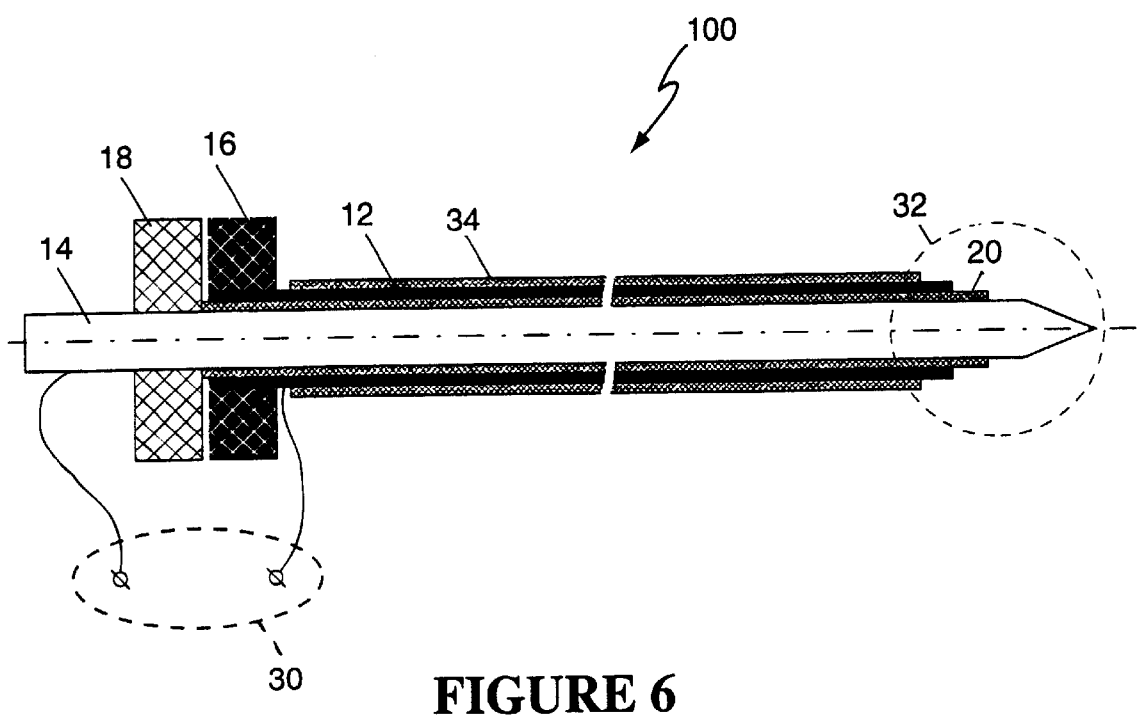
FIG. 6 is a schematic illustration of a longitudinal cross-section of another exemplary embodiment of a trocar needle probe for electrical impedance measurements provided in accordance with the present invention.

This experiment was performed on a standard resistivity solution of 101.2 $\Omega$m at 1.0 MHz and the system was calibrated with the needle inserted 10 mm into the solution. As revealed by this experiment the depth of needle insertion does not play a significant factor in the resistivity measurement. For precise measurement, however, as an alternative to the configuration of FIG. 1, in accordance with an alternate embodiment of the invention, another insulation layer 34 is provided on the sleeve or barrel 12 of the two-part needle 100, as shown in FIG. 6.

In accordance with this alternate configuration, the barrel 12 of the needle 100 is covered with an insulated layer 34 in a manner similar to the insulation of stylet 14 with layer 20. Note that layer fills the diametrical gap between barrel 12 and stylet 14 so that no fluid or other material can pass into that gap and change the effective area of the barrel electrode. In this way, the area of the barrel electrode is independent of the needle depth of insertion into the substance/tissue. Experiments with this needle design revealed constant resistivity measurements while varying the insertion depth. Consequent layers of barrels and insulators may be added to the design in the same fashion in order to provide additional electrodes at the needle tip.

The needle impedance probe may be used to assess the nature of the substance/tissue at the needle tip through electrical impedance/resistivity/conductivity measurements. In particular the probe may be used to distinguish between different types of tissue that the needle tip passes while inserting the needle. This is useful for the confirmation of insertion into a known resistivity target and for diagnostic purposes where tissue/substance nature is determined by correlating resistivity values.

The inventors have used the probe to assess the presence of cancer cells at the needle tip for diagnostic and "smart" biopsy purposes. In this way cancer tumors not visible on radiographic images may be detected and localized. As can be appreciated, followed by a localized therapy, this process could open a new domain for cancer therapy.

Figure 7:
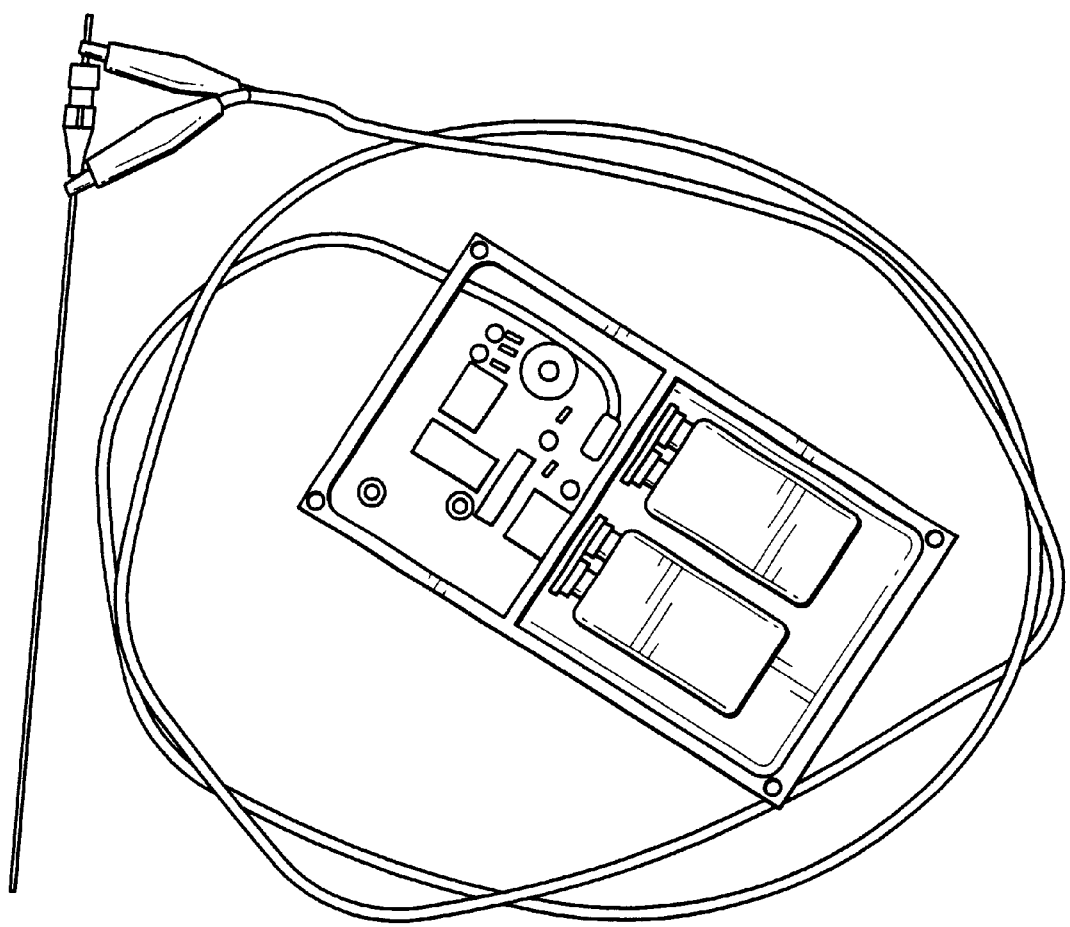
FIG. 7 is a photo of an exemplary needle-probe and impedance meter used for percutaneous renal access in accordance with the invention.

The inventors have also used the needle sensor for the confirmation of needle insertion into the renal collecting system in image guided percutaneous procedures. Percutaneous renal procedures commonly commence by obtaining access to the collecting system of the kidney with a trocarneedle. Currently, percutaneous renal access in the operating room is performed using free hand needle placement guided by "C-arm" fluoroscopy. Surgeons have limited objective means to assess whether successful access was obtained. The needle-probe was successfully used to confirm needle insertion into the renal pelvis by verifying that the impedance of the substance at the tip of the needle matches the impedance of urine. The resistivity of urine is clearly distinct from the resistivity of the kidney and surrounding tissues and blood. This allowed the inventors to use for this application the simplest needle design (FIG. 1), in conjunction with a very simple impedance meter. The needle-probe and impedance meter used in that procedure are shown in FIG. 7.

Although the present invention has been described in particular with reference to use in monitoring renal access, for example, it is to be understood that one skilled in the art could adapt the impedance probe of the invention for use in other medical procedures in which a probe is inserted into tissues where it is necessary to distinguish between tissue types, e.g., to confirm arrival of the probe at a target site. For example, the impedance probe of the invention may be used for needle biopsy. In this example, it is important to know when the biopsy needle has reached the tumor tissue. Since tumor tissue in many cases has a different impedance than normal tissues, the needle probe of the invention may be used to ensure that the biopsy needle has actually located at the tumor site, thus optimizing the location of biopsy sampling.

Although the stylet and trocar sleeve have each been characterized as formed from a conductive material, it is to be understood that as an alternative to forming an entirety of such structures from an electrically conductive material, an electrically conductive material can be provided as a portion of the respective structures, so as to have a suitable portion exposed, e.g., at the distal tip for providing the requisite electrode for impedance measurement.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A surgical probe for obtaining impedance measurements, comprising:
    a hollow trocar sleeve having a proximal end portion, a distal end, a first electrically conductive portion defining a first electrode adjacent said distal end, and means for electrically connecting said first electrically conductive portion to said proximal end portion;
    a stylet having a proximal end portion, a distal end, a second electrically conductive portion defining a second electrode adjacent said distal end, and means for electrically connecting said second electrically conductive portion to said proximal end portion, said stylet being housed within said trocar sleeve;

an electrical insulator disposed between said trocar sleeve and said stylet; and impedance meter means operatively coupled to said proximal end portion of each of said trocar sleeve and said stylet so as to be electrically coupled to said first and second electrodes, for indicating the impedance of a biological substance contacting said electrodes.

2. A surgical probe as in claim 1, wherein said distal end of said stylet has a sharp, pointed tip.

3. A surgical probe as in claim 1, wherein said electrical insulator comprises a sleeve of insulating material disposed on said stylet, wherein said stylet is selectively slidably removable from said trocar sleeve, and wherein said sleeve of insulating material is removable from said trocar sleeve with said stylet.

4. A surgical probe as in claim 1, wherein said trocar sleeve is formed from an electrically conductive material whereby said means for electrically connecting said first electrically conductive portion to said proximal end portion comprises a wall of the trocar sleeve intermediate said proximal end portion and said distal end thereof.

5. A surgical probe as in claim 1, wherein said stylet is formed from an electrically conductive material whereby said means for electrically connecting said second electrically conductive portion to said proximal end portion comprises a main body of the stylet intermediate said proximal end portion and said distal end thereof.

6. A surgical probe as in claim 1, further comprising an electrical lead extending from said proximal end portion of each of said stylet and said trocar sleeve, and wherein said impediance meter is electrically coupled to said electrical leads.

7. A surgical probe as in claim 1, further comprising a layer of insulating material disposed in surrounding relation to said trocar sleeve, proximal of said first electrode, so as to electrically insulate the trocar sleeve, proximal of said first electrode, from a material into which the probe has been inserted.

8. A method for determining the position of a probe in tissue, comprising the steps of:

providing an impedance probe including a hollow needle barrel having a proximal end portion, a distal end, a first electrically conductive portion defining a first electrode adjacent said distal end, and means for electrically connecting said first electrically conductive portion to said proximal end portion; a stylet having a proximal end portion, a distal end, a second electrically conductive portion defining a second electrode adjacent said distal end, and means for electrically connecting said second electrically conductive portion to said proximal end portion, said stylet being slideably housed within said needle barrel; and an electrical insulator disposed between said needle barrel and said stylet; and impedance meter means operatively coupled to said proximal end portion of each of said needle barrel and said stylet so as to be electrically coupled to said first and second electrodes, for indicating the impedance of a biological substance contacting said electrodes;

inserting the impedance probe into a patient's body;

measuring the impedance between two points in a biological substance at a distal tip of said probe, corresponding to said first and second electrodes; and determining the location of the distal tip of said probe by monitoring the measured impedance.

9. A method as in claim 8, further comprising identifying the biological substance from the measured impedance.

10. A diagnostic impedance measuring system comprising:

an elongate tissue-penetrating needle having a distal end and a proximal end;

a first portion of said distal end of said tissue penetrating needle being electrically conductive;

at least one electrode structure mounted to the needle and disposed adjacent the distal end of the needle and axially spaced from said first portion thereof, said first portion and said at least one electrode being electrically connected to an impedance measuring device for measuring an electrical impedance of a biological substance contacting said first portion and said electrode.

11. A diagnostic impedance measuring system as in claim 10, wherein said electrically conductive electrode structure comprises a sleeve sized to be slidably received on said tissue-penetrating needle, at least a distal portion of said sleeve being electrically conductive; and further comprising an insulating material disposed between said first portion of said tissue-penetrating needle and said electrically conductive distal portion of said sleeve.

12. An impedance-based method for monitoring a position of a surgical needle comprising the steps of:

providing a needle probe comprising a hollow sleeve and a tissue piercing stylet slidably received therewithin, said stylet being formed from an electrically conductive material whereby a distal end thereof defines a first electrode structure, at least a distal portion of said sleeve comprising an electrically conductive material thereby defining a second electrode structure, said first and second electrodes being electrically insulated from one another;

electrically connecting said electrodes to an impedance meter;

inserting said needle into a patient, toward a target anatomical structure; and monitoring during said insertion step the impedance between the two electrodes.

13. A method as in claim 12, further comprising determining a location of the distal end of the needle probe from the measured impedance.

14. A method as in claim 12, further comprising identifying the biological substance adjacent the distal end of the needle probe from the measured impedance.

* * * * *